United States Patent [19]

Zhong et al.

[11] Patent Number: 5,582,578
[45] Date of Patent: Dec. 10, 1996

[54] METHOD FOR THE COMMINUTION OF CONCRETIONS

[75] Inventors: Pei Zhong; Franklin H. Cocks, both of Durham; Glenn M. Preminger, Chapel Hill, all of N.C.

[73] Assignee: Duke University, Durham, N.C.

[21] Appl. No.: 509,770

[22] Filed: Aug. 1, 1995

[51] Int. Cl.⁶ .................................................. A61B 17/22
[52] U.S. Cl. .............................. 601/4; 128/660.03; 601/2; 604/22
[58] Field of Search .................................. 310/334, 322, 310/337, 335; 601/2, 3, 4; 128/660.03; 607/97; 604/20, 22

[56] References Cited

U.S. PATENT DOCUMENTS

| | | |
|---|---|---|
| 3,942,531 | 3/1976 | Hoff et al. . |
| 4,655,220 | 4/1987 | Hahn et al. . |
| 4,664,111 | 5/1987 | Reichenberger . |
| 4,821,730 | 4/1989 | Wurster et al. . |
| 4,888,746 | 12/1989 | Wurster et al. . |
| 5,209,221 | 5/1993 | Riedlinger . |
| 5,219,401 | 6/1993 | Cathignol et al. . |

FOREIGN PATENT DOCUMENTS 3921808  1/1991  Germany .

*Primary Examiner*—Marvin M. Lateef
*Assistant Examiner*—Shawna J. Shaw

[57] ABSTRACT

The invention relates to a method for the comminution of concretions in vivo by controlled, concentrated cavitation energy. This method utilizes two shock wave pulses with a specified time delay and pressure relationship, with the first shock wave pulse being used to induce a transient cavitation bubble cluster near the target concretion, and the second shock wave pulse to control and force the collapse of the cavitation bubble cluster towards the target concretion with concentrated energy deposition, while avoiding injury to surrounding tissue caused by random collapse of the cavitation bubbles. This invention makes it possible to significantly enhance the fragmentation efficiency of the concretion using shock waves while reducing potential deleterious injury to surrounding tissue.

12 Claims, 4 Drawing Sheets

METHOD FOR THE COMMINUTION OF CONCRETIONS

FIELD OF THE INVENTION

The present invention relates to a method for disintegration of concretions in vivo with reduced tissue injury, by the forced concentration of acoustically induced transient cavitation energy towards the target concretion.

BACKGROUND OF THE INVENTION

Comminution of concretions in vivo using extracorporeally generated shock waves (lithotripsy) is a recent medical practice, particularly in the treatment of urinary stone and biliary stone disease. Prior art describes various devices and methods for generating high-intensity, focused shock waves for the fragmentation of concretions inside a human being. U.S. Pat. No. 3,942,531 by Hoff, et al. discloses the use of a spark gap discharge in water to generate a shock wave within an ellipsoidal reflector which couples and focuses the shock wave to fragment kidney stones inside the body. Hahn, et al. in U.S. Pat. No. 4,655,220 disclose a device using a coil and a mating radiator, in the form of spherical segment, to produce magnetically induced self-converging shock waves. Wurster, et al. in U.S. Pat. Nos. 4,821,730 and 4,888,746, disclose the use of piezoelectric elements arranged in mosaic form on a spheroidal cap to produce focused high-intensity shock waves at the geometric center of the cap, where the concretion must be placed.

Despite the different principles used for shock wave generation, all these devices produce shock waves of a similar waveform, which can be characterized by a compressive phase consisting of a rapid shock front with a positive peak pressure up to 100 MPa, followed by a rarefaction (negative) phase with a negative peak pressure up to 10 MPa and with a few microseconds duration. It is also well known in the art that the negative phase of an incident shock wave can induce transient cavitation bubbles in the focal region.

It is further known in the art that when cavitation bubbles collapse near a stone surface, microjets will be produced due to the asymmetric collapse of the cavitation bubbles. These microjets impinge violently onto the stone surface and cause stone fragmentation. Experiments have shown that using the same shock wave generator at the same intensity level, a stone immersed in glycerol (a cavitation inhibitive medium) will not be damaged, while the same stone immersed in an aqueous solution such as water (a cavitation promotive medium) can be fragmented, despite the fact that the transmission of the shock wave energy in both cases is the same. It is established in the art that shock wave induced cavitation and the resultant microjet impingement is the primary mechanism for stone fragmentation. Furthermore, when shock wave-induced cavitation bubbles collapse near tissue surfaces, they can cause tissue injury through shock wave emission, the generation of high-temperatures, microjets, and the shear stresses associated with rapid bubble oscillation.

The present invention is based upon the discovery that the collapse of a cavitation bubble cluster can be controlled so as to cause increased concretion comminution by imposing an impinging shock wave of appropriate shape and intensity to collapse the bubble cluster from its outer layer into an inner layer collectively.

The collapse of a cavitation bubble by an impinging shock wave is found to be asymmetric, leading to the formation of a liquid jet which travels along the direction of the impinging shock wave. When occurring in water the liquid jet will be a water jet. It has been discovered that the collapse of a cavitation bubble can be controlled and guided by an incident shock wave, provided that this shock wave is applied at the correct time in the life of a cavitation bubble. It is further known in the art that the collapse of a cavitation bubble cluster by an impinging shock wave can concentrate 80% to 90% of the cavitation bubble energy from an outer layer to an inner layer, when these cavitation bubbles are forced to collapse in sequence by the incident shock wave. This concerted, controlled collapse of a cavitation bubble cluster by an impinging shock wave is found to produce an efficient concentration of the cavitation energy towards the center of the bubble cluster, where the concretion is located. Because the cavitation energy is directed towards and concentrated on the target concretion, tissue injury associated with the comminution of the concretion is reduced. Therefore, the comminution of concretions in vivo utilizing controlled, concentrated cavitation energy has the advantage of increased fragmentation efficiency with reduced tissue injury.

Riedlinger, in U.S. Pat. No. 5,209,221, discloses a device for generating sonic signals for limiting, preventing or regressing the growth of pathological tissue in vivo. The sonic signal, consisting of at least one rarefaction phase with a negative sonic pressure amplitude with a value greater than $2 \times 10^5$ Pa, is radiated with a carrier frequency exceeding 20 kHz, a sonic pulse duration, T, of less than 100 microseconds and a pulse recurrence rate of less than 1/(5T). Thus, the time delay between two adjacent sonic pulses is greater than 500 microseconds. Since experiments have shown that the transient cavitation bubble clusters generated by all current lithotripsy devices last less than 400 microseconds, it is clear that by using the sonic pulse sequence as disclosed by Riedlinger, the ensuing sonic pulses will not be able to control the collapse of the cavitation bubble cluster induced by the initial sonic pulse.

Similarly, Cathignol, et al. in U.S. Pat No. 5,219,401 disclose an apparatus for the selective destruction of biological materials, including cells, soft tissues, and bones. The injection of gas bubble precursor microcapsules, having diameters preferably in the 0.5 to 300 microns range and made from materials such as lecithin, into the blood stream is used by Cathignol, et al. as the primary means of generating gas bubbles in vivo. Although the phenomenon of cavitation provoked by an ultrasonic wave generator working in a frequency range of $10^4$ to $10^5$ Hz is described, the sonic pulse sequence is not specified. As we have now discovered, the forced collapse of cavitation bubbles to produce fluid microjets for the enhanced comminution of concretions requires a specified relationship between the first, cavitation-inducing, acoustic pulse and the second, cavitation-collapsing, acoustic pulse. In addition, we have now also discovered that the second, cavitation-collapsing, acoustic pulse must have a compressive (positive) phase with a long duration and only a small, or no, tensile (negative) component.

Reichenberger, in U.S. Pat. No. 4,664,111, discloses a shock wave tube for generating time-staggered shock waves by means of a splitting device, such as a cone, for the fragmentation of concrements in vivo. Reichenberger discloses that the effects of the shock waves can be improved if they are so closely spaced in time that they overlap in their action on the concrement. The effects of shock wave induced cavitation are not considered or mentioned by Reichenberger.

None of the prior art teaches the use of a secondary shock wave, imposed at a specified time delay, to control the collapse of a transient cavitation bubble cluster induced by a primary shock wave. Without this time sequenced second shock wave, it has now been discovered that the efficiency of comminuting concretions in vivo by shock wave lithotripsy will be low, and the concomitant risk for tissue injury due to the uncontrolled cavitation energy deposition during the procedure will be correspondingly increased.

In the presently disclosed spark gap (electrohydraulic), electromagnetic, and piezoelectric shock wave generators, cavitation bubbles are formed after the passage of the incident shock wave. Furthermore, the shock wave-induced cavitation bubble clusters are transient, lasting for less than 400 microseconds, a time much shorter than the interval of shock wave delivery. Therefore, in presently used lithotripsy devices the collapse of the transient cavitation bubble cluster occurs in an uncontrolled, random fashion, resulting in only a small portion of the collapsing energy, typically less than 10%, being transmitted towards the stone surface. Much of the cavitation energy is either dissipated or consumed by surrounding tissue. Consequently, large numbers of shock waves are needed for adequate stone fragmentation, and as a consequence concomitant tissue injury is also produced by current shock wave generators. Using present lithotripsy devices, more than 4,000 pulses may be needed to produce desired stone comminution, while significant tissue damage may accompany this process.

The disclosed prior art uses uncontrolled, shock wave-induced cavitation for the fragmentation of concretions in vivo. Because cavitation bubble collapse is uncontrolled in devices disclosed by the prior art, the fragmentation efficiency is low, and thus the number of required acoustic pulses for producing adequate stone comminution is high. Furthermore, the method and apparatus of the prior art has a high risk for tissue injury due to the random deposition of the cavitation energy to adjacent tissue when the cavitation bubbles collapse.

SUMMARY AND OBJECTIVES OF THE INVENTION

The present invention provides a method for generating a sequence of shock wave pulses with a specified very short time delay (less than 400 microseconds), and with pressure relationships between the individual pulses that provide both a means of inducing a transient cavitation cluster, and a means of controlling the growth and subsequent collapse of the cavitation bubble cluster near the target concretions in vivo, to achieve increased fragmentation efficiency with reduced tissue injury.

It is an objective of the present invention to provide a method of using controlled, concentrated collapse of cavitation bubbles for effective comminution of concretions in vivo with reduced injury to surrounding tissue.

A further objective of the present invention is to produce controlled, concentrated cavitation bubble collapse by using a sequence of shock wave pulses with a specified time delay and with specified pressure relationships between the sequential shock wave pulses, and to use an initial shock wave pulse for inducing a transient cavitation bubble cluster near the target concretion, while using a subsequent shock wave pulse to force and control the collapse of the cavitation bubble cluster towards the target concretions in vivo.

It is yet another objective of the present invention to measure acoustic emission produced by the transient cavitation bubble cluster, induced by the incident shock waves, to provide a means of determining the time delay required between a first and a second shock wave pulse in order to increase the effectiveness of cavitation energy in the comminution of concretions in vivo.

It is still another objective of the present invention to use shock wave pulses propagating along different pathways through interposed living tissue before converging at the target concretion to minimize cavitation-induced tissue injury along the shock wave pathway while maximizing the shock wave-bubble interaction at the target concretion for improved comminution efficiency with reduced tissue injury.

BRIEF DESCRIPTION OF THE DRAWINGS

The objectives and features of the present invention will become apparent from the following description and appended claims taken in conjunction with the accompanying drawings.

DETAILED DESCRIPTION OF THE PREFERRED EMBODIMENTS

Figure 1:
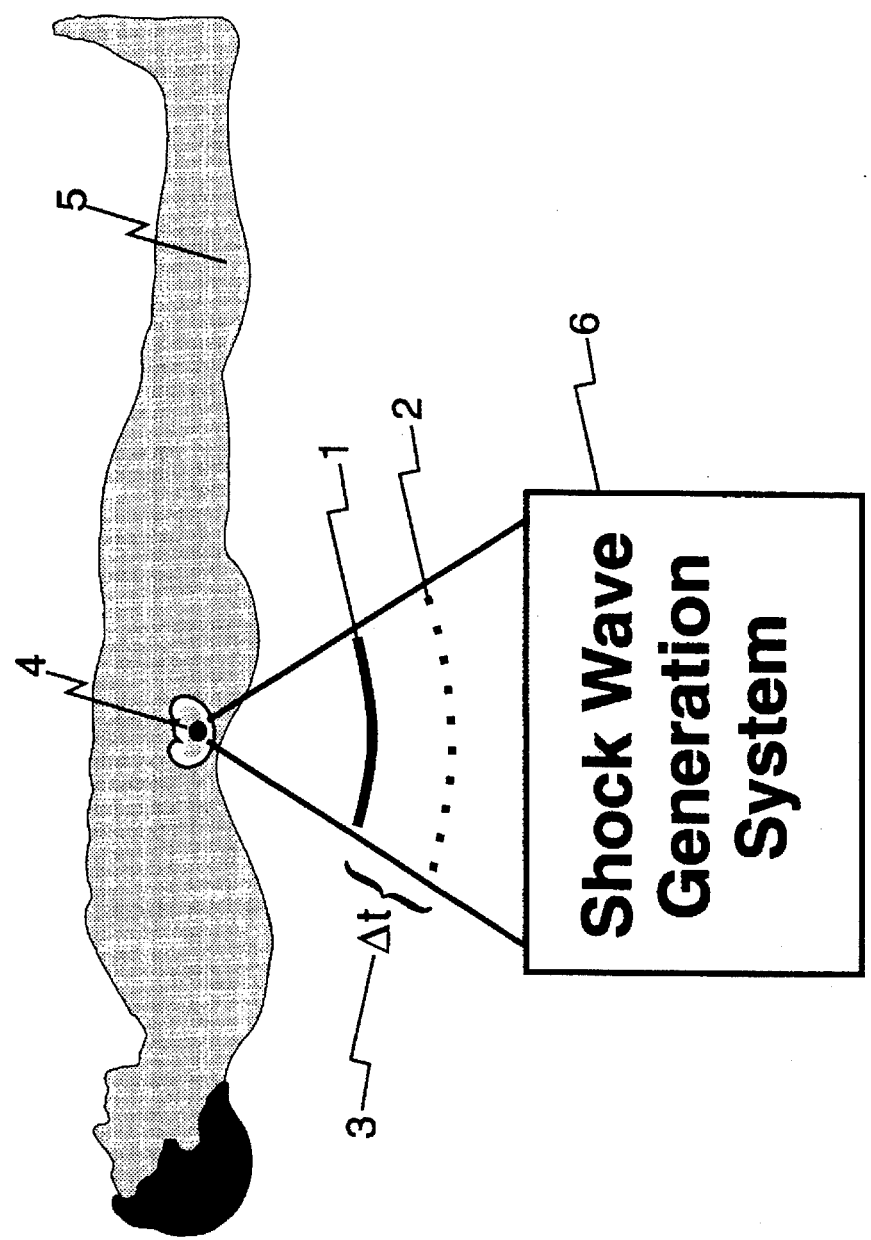
FIG. 1 shows a concretion in a living body and a shock wave generation system generating two shock wave pulses in sequence separated by a specified time delay for the comminution of concretions inside a living body.

According to a first preferred embodiment of the present invention, FIG. 1 shows a method of using two shock wave pulses 1, 2 separated by a specified time delay ∆t 3. The shock wave pulses 1, 2 are produced by a shock wave generation system 6 and aimed confocally at a target concretion 4 inside a living being 5, for the comminution of the target concretion 4 with improved fragmentation efficiency and reduced tissue injury. These two pulses consist, respectively, of a first shock wave pulse 1 and second shock wave pulse 2, separated in time by a time delay ∆t 3. We have now discovered that for optimal effect, this should be 50 to 400 microseconds (µs).

Figure 2:
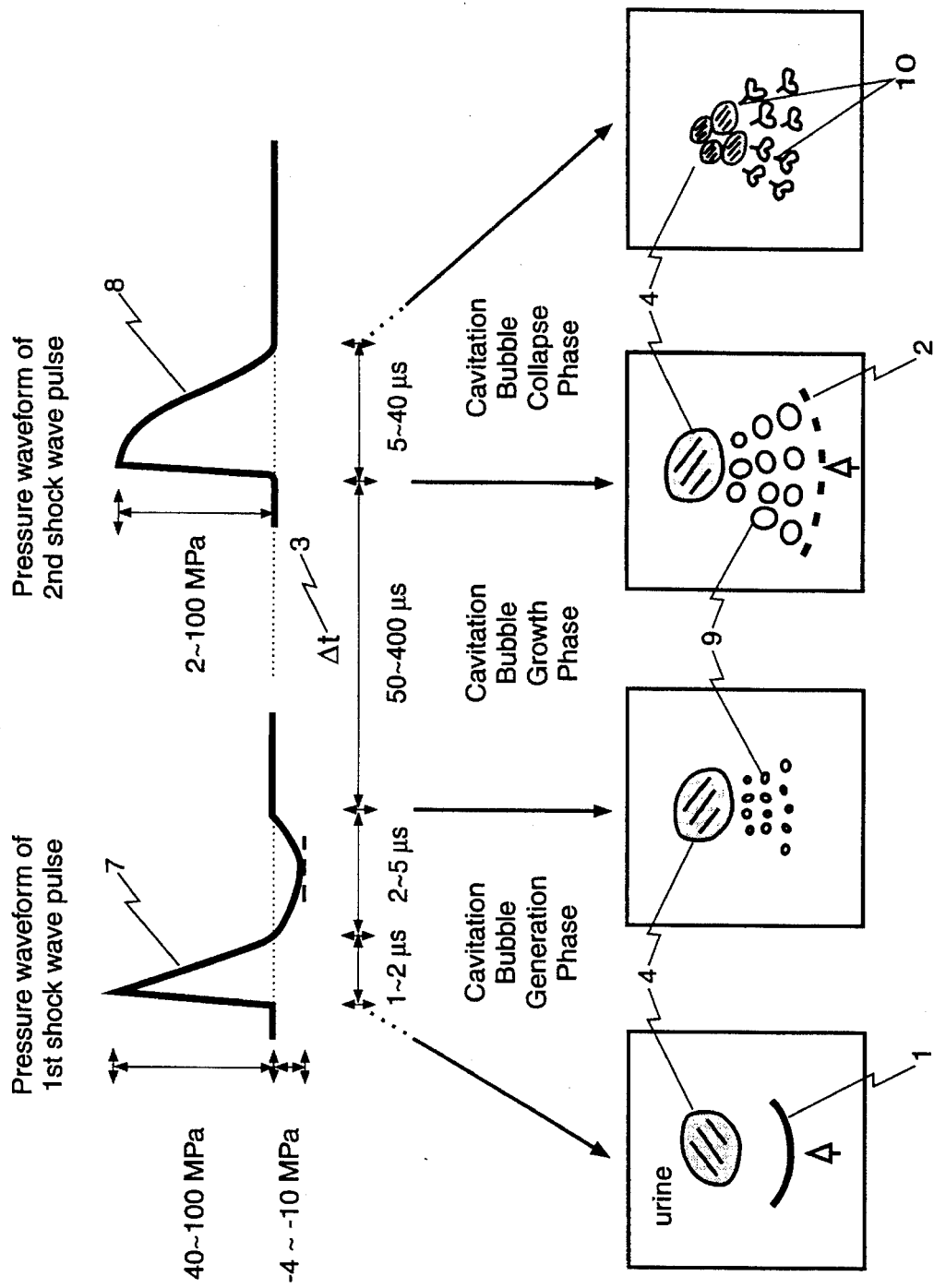
FIG. 2 shows two shock wave pulses in sequence separated by a specified time delay of 50 to 400 microseconds (µs) to induce, by the tensile phase of the first shock wave pulse, a transient acoustic cavitation bubble cluster near a target concretion and to collapse, by the second shock wave pulse, the induced cavitation bubble cluster after it expands to its maximum size, to concentrate the cavitation energy in the form of liquid microjets towards the target concretion for improved fragmentation efficiency with reduced tissue injury.

According to another preferred embodiment of the present invention as illustrated in FIG. 2, the pressure waveform 7 of the first shock wave pulse 1 consists of a compressive phase with a positive peak pressure amplitude in the 20 to 100 million pascals (MPa) range and with a positive duration of 1 to 2 microseconds, followed by a tensile phase with a negative peak pressure amplitude of minus 1 to minus 10 MPa and with a duration of 2 to 5 microseconds. The pressure waveform 8 of the second shock wave pulse 2 consists of essentially a compressive phase with a positive peak pressure amplitude of 2 to 100 MPa and a duration of 5 to 40 microseconds. It has now been discovered that the time delay $\Delta t3$ between the first shock wave pulse 1 and the second shock wave pulse 2 should be in a range of 50 to 400 microseconds for achieving improved stone comminution and reduction in tissue damage.

According to another advantageous embodiment of the present invention as shown in FIGS. 1 and 2, the tensile phase of the first shock wave pulse 1 is used to induce a transient cavitation bubble cluster 9 near a concretion 4 surface, with the induced cavitation bubble cluster 9 growing to its maximum size in 50 to 400 microseconds, depending on the intensity of the first shock wave pulse 1. The second shock wave pulse 2, separated from the first shock wave pulse 1 by a specified time delay is used to collapse the cavitation bubble cluster 9 at its maximum expansion, leading to a concerted collapse of the cavitation bubble cluster 9 towards the target concretion 4. This forced collapse has now been found to result in the formation of high-speed liquid jets 10 impinging towards the target concretion 4 and to cause disintegration of the stone 4 with increased rapidity as compared to the uncontrolled collapse of the cavitation bubble cluster.

According to another preferred embodiment of the present invention, the first shock wave pulse 1 can be generated by an electrohydraulic device, utilizing a spark gap discharge in water within an ellipsoidal reflector, such as the apparatus disclosed by Hoff, et al in U.S. Pat. No. 3,942,531. Electromagnetic shock wave generators, well known to those skilled in the art may also be used, such as the apparatus disclosed by Hahn, et al. in U.S. Pat No. 4,655,220. In addition, piezoelectric shock wave generators as equally well known to those skilled in the art may also be used, such as the apparatus disclosed by Wurster, et al. in U.S. Pat No. 4,821,730. These previously disclosed devices generate a distribution of high-intensity shock waves in a focal volume embracing the target concretions 4. It is well known in the art that the beam diameter of the shock wave pulses in the focal plane and the depth of focus along the shock wave axis are in the range of 2 to 15, and 12 to 120 mm, respectively. It has now been discovered that the transient cavitation bubble cluster, induced by these devices, is distributed in a volume between 1.4 and 65 cubic centimeters.

According to another advantageous embodiment of the present invention, the second shock wave pulse 2 can be generated piezoeletrically by the superposition of individual shock wave pulses of different amplitudes, frequencies and phases, as disclosed by Wurster, et al. in U.S. Pat. No. 4,888,746. Wurster, et al. disclose a focussing ultrasound transducer comprising of mosaic assemblies of piezoelectric materials mounted on an inner surface of a spherical cap, with the energizing of individual piezoelectric elements being controlled electronically. Moreover, Wurster, et al. disclose that by energizing in a particular sequence an array of piezoelectric elements, in such a manner that the negative halfwaves of the sound waves generated at the active transducer surface by momentary reverse oscillation of the transducer areas energized in each case may be balanced by an energizing in phase opposition of other transducer elements, meaning that a positive pressure surge only will be generated at the focal point.

Figure 3:
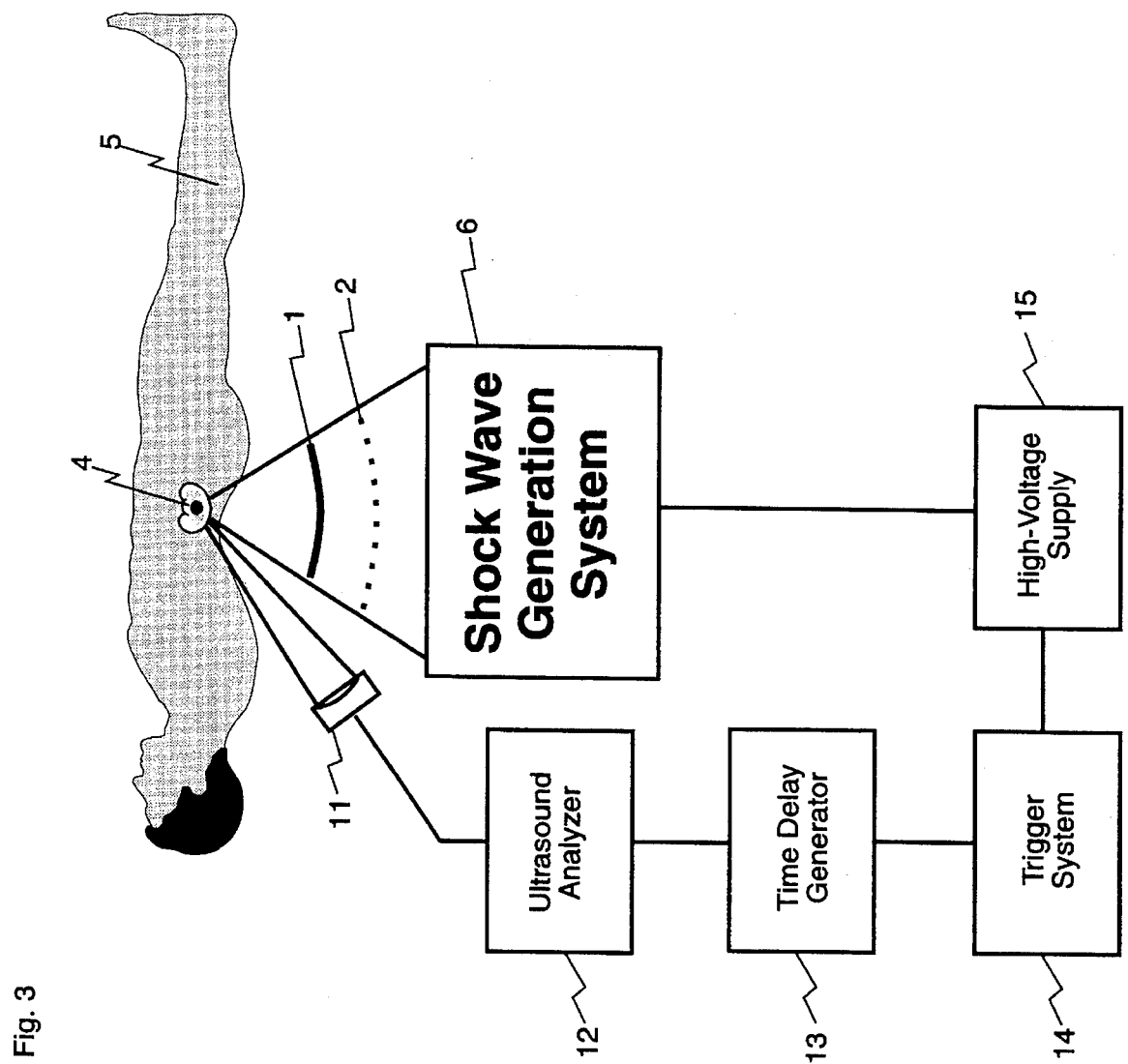
FIG. 3 shows the detection of acoustic emission produced by the first expansion, subsequent partial collapse and ensuing rebound of a transient cavitation bubble cluster, induced by the first shock wave pulse from a shock wave generation system, to determine closely and accurately the time delay required for the delivery of the second shock wave pulse required to collapse the transient acoustic bubble cluster at its maximum size, to comminute a concretion within a living body.

According to a further embodiment of the present invention, FIG. 3 shows a method for measuring acoustic emission, generated by the transient cavitation bubble cluster 9 induced by the first shock wave pulse 1, by using a passive cavitation detector 11, positioned outside a living body 5 and aligned confocally with the focal point of a shock wave generation system 6. The passive cavitation detector 11, consisting of one or an array of focussed piezoceramic transducers, with a resonant frequency in the range of 100 KHz to 10 MHz, and a focal length of 4 to 8 inches, is connected to an ultrasound analyzer 12. The shock wave generation system 6 initially is set-up to produce a test shock wave pulse with the same pressure waveform as that of the first shock wave pulse 1, which induces a transient cavitation bubble cluster 9 around the focal point of the shock wave generation system 6. By detecting the acoustic emission produced by the initial expansion, subsequent collapse and immediate rebound of the cavitation bubble cluster 9 using the passive cavitation detector 11, and by analyzing the acoustic emission signals using the ultrasound analyzer 12, the duration of the growth of the transient cavitation bubble cluster 9 can be determined. Subsequently, this information can then be used to set the time delay generator 13, connected to a trigger system 14 and a high-voltage supply 15, to control the shock wave generation system 6 to produce the first shock wave pulse 1 and the second shock wave pulse 2 in sequence with a specified time delay so that the transient cavitation bubble cluster 9 induced by the first shock wave pulse 1 can be forced to collapse at its maximum size by the second shock wave pulse 2, thus concentrating substantially all of the cavitation energy towards the target concretion 4 for improved stone comminution with reduced tissue injury.

Figure 4:
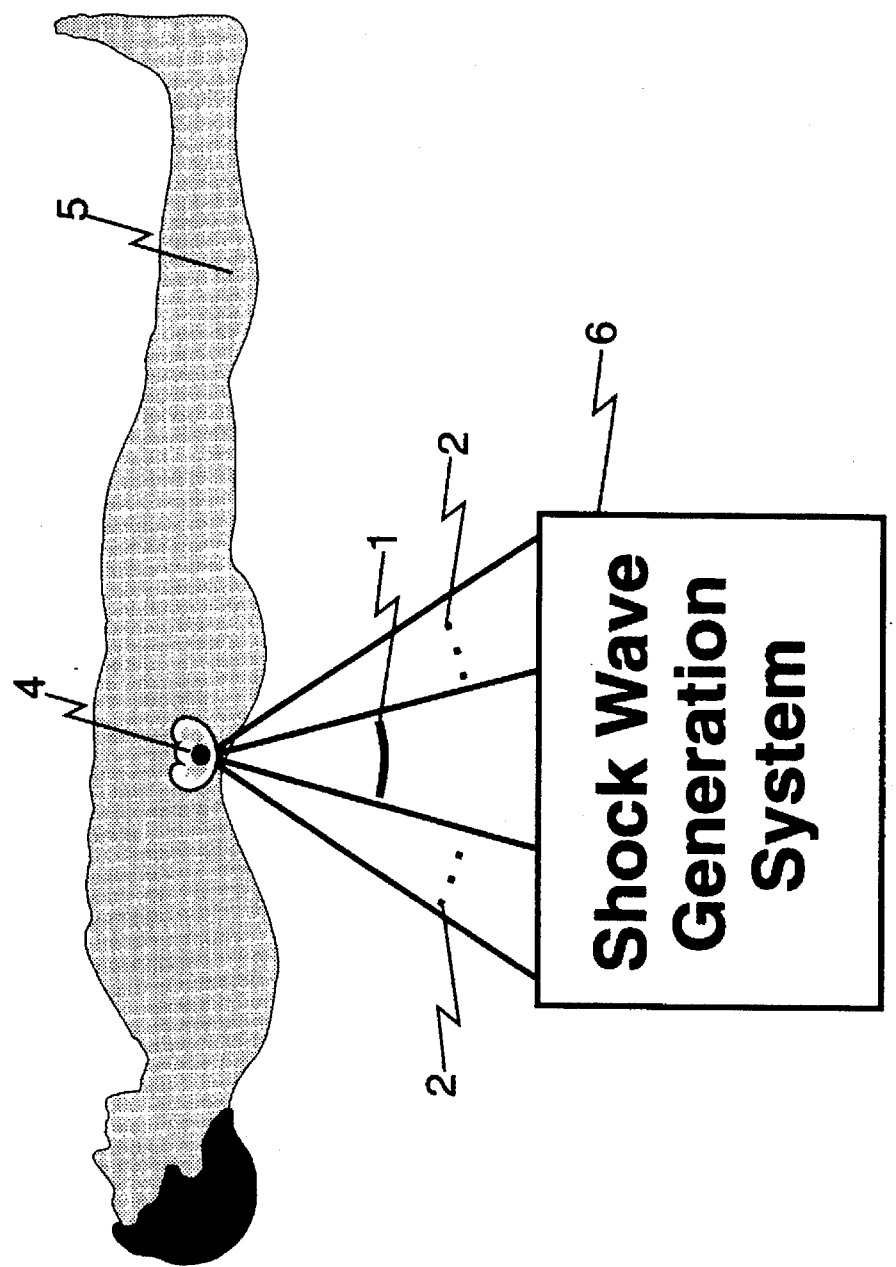
FIG. 4 shows two shock wave pulses propagating along different pathways through interposed tissue in a living body before converging at the target concretion.

According to yet another embodiment of the present invention as shown schematically in FIG. 4, the first shock wave pulse 1 and the second shock wave pulse 2, as generated by any of the abovementioned means, can be sent in such a configuration that these shock wave pulses propagate along different pathways in the interposed tissue before arriving at the target concretion 4. Thus these two shock wave pulses have a common focus, and this focus is at or near the target concretion 4. A particular advantage of this embodiment is that the first shock wave pulse 1 and the second shock wave pulse 2 will not interact with each other along the interposed tissue pathway. Therefore, intensive shock wave-cavitation bubble interaction will not occur in the interposed tissue along the shock wave pathways, but will be produced near the target concretion 4. Hence, this embodiment has the advantage of enhancing stone fragmentation efficiency with reduced tissue injury.

It will be obvious to those skilled in the art that many modifications may be made within the scope of the present invention without departing from the spirit thereof. The present method may be applied to the treatment of ureteral stones, bladder stone, gallstones, and other concretions located within a living body in addition to kidney stones.

We claim:

1. A method for comminuting concretions located within a living body, said method consisting essentially of the steps of (a) producing a first shock wave pulse in a liquid, said first shock wave pulse having a compressive phase with a peak amplitude whose magnitude is greater than 20 million pascals and with a duration of 1 to 2 microseconds, and said first shock wave pulse having a tensile phase with a peak amplitude whose magnitude is greater than 1 million pascals and with a duration of 2 to 5 microseconds, (b) focussing said first shock wave pulse to produce a transient cavitation bubble cluster in a volume embracing said concretions, said volume being less than 65 cubic centimeters, (c) producing a second shock wave pulse in said liquid, said second shock wave pulse being produced after a time delay that is between 50 and 400 microseconds after said first shock wave pulse, said second shock wave pulse having a compressive phase with a peak amplitude whose magnitude is between 2 and 100 million pascals and with a duration between 2 and 40 microseconds, (d) focussing said second shock wave pulse in said volume, whereby said transient acoustic cavitation bubble clusters are forced to collapse by said second shock wave pulse thereby producing liquid jets, said jets impinging on said concretions, whereby said concretion comminution is increased.

2. A method as disclosed in claim 1, wherein said first acoustic pulse is produced by means of a shock wave generation system selected from the group of shock wave generation systems consisting of electrohydraulic, electromagnetic, and piezoelectric shock wave generation systems.

3. A method as disclosed in claim 1, wherein said second shock wave pulse is produced by means of the superposition of shock wave pulses of different amplitudes, frequencies, and phases, produced by energizing of an array of piezoelectric elements mounted on an inner surface of a spherical cap with said energizing of said piezoelectric elements being controlled electronically.

4. A method as disclosed in claim 1, wherein said liquid is water and said liquid jets are water jets.

5. A method for comminuting concretions located within a living body, separated from a surface of said living body by interposed tissue, said method consisting essentially of the steps of (a) producing a test shock wave pulse in a liquid, said test shock wave pulse having a compressive phase with a peak amplitude whose magnitude is greater than 20 million pascals and with a duration of 1 to 2 microseconds, and said first shock wave pulse having a tensile phase with a peak amplitude whose magnitude is greater than 1 million pascals and with a duration of 2 to 5 microseconds, (b) focussing said test shock wave pulse to produce a test transient cavitation bubble cluster, said test transient cavitation bubble cluster producing an acoustic emission through an initial expansion, subsequent collapse and rebound of said test transient cavitation bubble cluster in a volume embracing said concretions, said volume being less than 65 cubic centimeters, (c) measuring said acoustic emission produced by said test transient cavitation bubble cluster, induced by said test shock wave pulse, and determining a duration of growth of said test transient cavitation bubble cluster, (d) producing a first shock wave pulse in said liquid, said first shock wave pulse having a compressive phase with a peak amplitude whose magnitude is greater than 20 million pascals and with a duration of 1 to 2 microseconds, said first shock wave pulse having a tensile phase with a peak amplitude whose magnitude is greater than 1 million pascals and with a duration of 2 to 5 microseconds, (e) focussing said first shock wave pulse to produce a transient cavitation bubble cluster in a volume embracing said concretions, said volume being less than 65 cubic centimeters, (f) producing a second shock wave pulse in sequence to said first shock wave pulse in said liquid, said second shock wave pulse having a compressive phase with a peak amplitude whose magnitude is between 2 and 100 million pascals and with a duration between 2 and 40 microseconds, said second shock wave pulse being produced at a specified time delay after said production of said first shock wave pulse, said specified time delay being equal to said duration of growth of said test transient cavitation bubble cluster, (g) focussing said second shock wave pulse in said volume, whereby said transient acoustic cavitation bubble clusters are collapsed by said second shock wave pulse thereby producing liquid jets, said jets impinging on said concretions, whereby said concretion is comminuted.

6. A method for comminuting concretions as disclosed in claim 5, wherein said acoustic emission is measured by using a passive cavitation detector, said duration of growth of said test transient cavitation bubble cluster being determined by an ultrasound analyzer.

7. A method for comminuting concretions as disclosed in claim 5, wherein said specified time delay between said production of said first shock wave pulse and said production of said second shock wave pulse, is determined using a time delay generator, a trigger system and a high-voltage supply connected with said shock wave generation system, based on said duration of growth of said test transient cavitation bubble cluster.

8. A method for comminuting concretions as disclosed in claim 5, wherein said liquid is water and said liquid jets are water jets.

9. A method for comminuting concretions located within a living body, said method consisting essentially of the steps of (a) producing a first shock wave pulse in a liquid, said first shock wave pulse having a compressive phase with a peak amplitude whose magnitude is greater than 20 million pascals and with a duration of 1 to 2 microseconds, and said first shock wave pulse having a tensile phase with a peak amplitude whose magnitude is greater than 1 million pascals and with a duration of 2 to 5 microseconds, (b) focussing said first shock wave pulse to produce a transient cavitation bubble cluster in a volume embracing said concretions with said volume being less than 65 cubic centimeters, (c) producing a second shock wave pulse in said liquid, said second shock wave pulse being produced after a time delay that is between 50 and 400 microseconds after said first shock wave pulse, said second shock wave pulse having a compressive phase with a peak amplitude whose magnitude is between 2 and 100 million pascals and with a duration between 2 and 40 microseconds, (d) sending said first shock wave pulse and said second shock wave pulse produced by said shock wave generation system along different pathways in said interposed tissue before arriving at said concretions, (e) focussing said second shock wave pulse in said volume, whereby said transient acoustic cavitation bubble clusters are forced to collapse by said second shock wave pulse thereby producing liquid jets, said jets impinging on said concretions, whereby said concretion is comminuted.

10. A method for comminuting concretions as disclosed in claim 9, wherein said first shock wave pulse and said second shock wave pulse propagate along coaxial pathways.

11. A method for comminuting concretions as disclosed in claim 9, wherein said first shock wave pulse and said second shock wave pulse propagate along said different pathways in said interposed tissue before arriving at a common focus which has a volume less than 65 cubic centimeters.

12. A method for comminuting concretions as disclosed in claim 9, wherein said liquid is water and said liquid jets are water jets.

* * * * *